United States Patent [19]

Szabadkai et al.

[11] Patent Number: 5,169,859
[45] Date of Patent: Dec. 8, 1992

[54] THIAZOLIDINONE DERIVATIVES, PHARMACEUTICAL COMPOSITIONS CONTAINING THEM AND PROCESS FOR PREPARING SAME

[75] Inventors: István Szabadkai; Kálmán Harsányi; Zsoltné Szabó; Béla Hegedüs; Elemér Ezer; Judit Matûz; Láslo Szporny; Katalin Sághy; György Hajós, all of Budapest; Attila Csehi, Göd; Gábor Balogh, Budapest, all of Hungary

[73] Assignee: Richter Gedeon Vegyeszeti Gyar RT, Budapest, Hungary

[21] Appl. No.: 730,922

[22] PCT Filed: Nov. 23, 1990

[86] PCT No.: PCT/HU90/00077
§ 371 Date: Jul. 18, 1991
§ 102(e) Date: Jul. 18, 1991

[87] PCT Pub. No.: WO91/08203
PCT Pub. Date: Jun. 13, 1991

[30] Foreign Application Priority Data
Nov. 24, 1989 [HU] Hungary ............... 6159/89

[51] Int. Cl.$^5$ ............... C07D 277/14; A01K 31/425
[52] U.S. Cl. ................ 514/369; 548/182; 548/186; 548/189
[58] Field of Search ............ 548/182, 186, 189; 514/369

[56] References Cited

U.S. PATENT DOCUMENTS 4,937,252  6/1990  Szabadkai ............ 548/182

FOREIGN PATENT DOCUMENTS 371733  6/1990  European Pat. Off. ........... 548/182

Primary Examiner—Robert Gerstl
Attorney, Agent, or Firm—Keil & Weinkauf

[57] ABSTRACT

The present invention relates to novel compounds of the general formula (I)

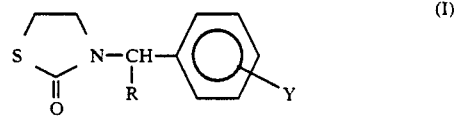

wherein
R means hydrogen or $C_{1-4}$ alkyl group; and
Y stands for cyano, trifluoromethyl, aryloxy or aryl($C_{1-4}$ alkyl)oxy group.

The compounds according to the invention show a gastric acid secretion-inhibiting effect and therefore, they are useful for the treatment of gastric and duodenal ulcers. In addition, they exert a cytoprotective action against gastric laesions induced, e.g. by indomethacin or acid-containing alcohol.

6 Claims, No Drawings

THIAZOLIDINONE DERIVATIVES, PHARMACEUTICAL COMPOSITIONS CONTAINING THEM AND PROCESS FOR PREPARING SAME

This invention relates to novel 2-thiazolidinone derivatives of the formula (I),

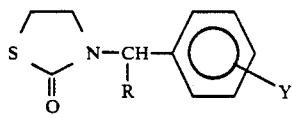

wherein
R means hydrogen or a $C_{1-4}$alkyl; and
Y stands for cyano, trifluoromethyl, aryloxy or aryl($C_{1-4}$alkyl)oxy group
as well as the pharmaceutical compositions containing these compounds.

The compounds of formula (I) possess a significant gastric acid secretion-inhibiting effect. They bear a high therapeutic importance since the number of patients suffering from gastric or duodenal ulcer is continuously increasing both in the absolute and relative sense as well.

Compounds, which are structurally similar to those of the formula (I) and exert a similar gastric acid secretion-inhibiting action, have been published in the Hungarian patent specification No. 198,915. The compounds being within the scope of this invention are substantially different from the known substances due to the nature of their substituents bound to the aromatic nuclei.

According to an other aspect of the invention, there is provided a process for the preparation of compounds of the formula (I)

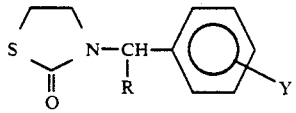

wherein
R means hydrogen or $C_{1-4}$alkyl group; and
Y stands for cyano, trifluoromethyl, aryloxy or aryl($C_{1-4}$alkyl)oxy group
which comprises reacting a compound of the formula (II)

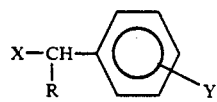

wherein R and Y are as defined above and X represents halogen, mesyloxy or tosyloxy group, with 2-thiazolidinone.

The reaction according to the process of the invention is carried out in a solvent, preferably in a $C_{3-8}$ ketone such as e.g. methyl isobutyl ketone, or in an aqueous ketone, dimethylformamide or dimethylsulfoxide, in the presence of an acid binding agent, preferably an alkaline metal carbonate or hydrogen carbonate. After filtering off or washing out the inorganic precipitate with water, the product obtained from the reaction is separated by filtration or, after removing the solvent, it is purified by recrystallization or column chromatography.

2-Thiazolidinone used as starting compound is known and can be prepared according to the literature [J. Am. Chem. Soc. 78, 5349 (1956); and J. Chem. Soc. 1952, 3094].

From the compounds of formula (II), the substance containing halogen as X is a commercially available fine chemical (see the concerning booklet of Aldrich); the substances containing mesyloxy group as X can be prepared from the corresponding alcohols by using a method described in the Hungarian patent specification No. 163,399.

Based on the pharmacological investigations 3-(2-cyanophenylmethyl)-2-thiazolidinone is an outstanding member of the compound class of formula (I). This compound shows a gastric acid secretion-inhibiting effect on the so-called Shay's rat [Shay: Gastroenterology 5, 43 (1945)] with an oral $ED_{50}$ value of 1.7 mg/kg. This compound is effective even against the indomethacin-induced gastric ulcer with an oral $ED_{50}$ value of 1.2 mg/kg; it is active also against gastric laesions induced by acid-containing alcohol [Robert: Gastroenterology 77, 761 (1979)], i.e. it exhibits a so-called cytoprotective effect with an oral $ED_{50}$ value of 3.7 mg/kg.

On the basis of our preliminary investigations, the expected human daily dose of the above compounds according to the invention amounts of 10–100 mg for one patient.

The preparation of the novel compounds according to the invention is illustrated by the general process described hereinafter:

To a mixture containing 3.09 g (0.03 mol) of 2-thiazolidinone, 11.2 g of potassium carbonate, 1.8 g of potassium hydrogen carbonate, 0.5 ml of water and 30 ml of methyl isobutyl ketone, 0.033 mol of a benzyl halide or benzyl alcohol mesylate or tosylate derivative of the formula (II) is added then the mixture is boiled under reflux till the complete consumption of the starting 2-thiazolidinone which is controlled by thin layer chromatography (TLC) by using a developing system of benzene/methanol/glacial acetic acid in a 10:3:1 ratio. After cooling down the reaction mixture is stirred with 30 ml of water for 30 minutes. An eventually remaining insoluble part is filtered off, washed with water, dried and purified by recrystallization. The filtrate as a second generation can be worked up in the following way:

When two clear phases appear on the effect of water, the organic layer is separated, washed with 30 ml of water, the organic phase is dried and evaporated. The residue is purified by column chromatography (on Kieselgel 60, 230-400 mesh, by using chloroform or ethyl acetate as eluent) or by recrystallization.

The compounds and their most important characteristics prepared as described above are summarized in Table I without any restriction of the scope of the invention to the Examples.

The chemical names of compounds listed in Table I are as follows:
1. 3-(2-cyanophenylmethyl)-2-thiazolidinone,
2. 3-(4-cyanophenylmethyl)-2-thiazolidinone,
3. 3-(3-cyanophenylmethyl)-2-thiazolidinone,
4. 3-(1-phenyl-1-ethyl)-2-thiazolidinone,
5. 3-(3-phenoxyphenylmethyl)-2-thiazolidinone,
6. 3-(4-benzyloxyphenylmethyl)-2-thiazolidinone, 7. 3-(4-trifluoromethylphenylmethyl)-2-thiazolidinone,
8. 3-(2-trifluoromethylphenylmethyl)-2-thiazolidinone and
9. 3-(3-trifluoromethylphenylmethyl)-2-thiazolidinone.

-continued

| Ingredients: | g |
|---|---|
| Colloidal silicic acid | 1 |

TABLE I

| Compound No. | Empirical formula, Molecular weight | Yield % | Melting point °C. (cryst. solvent) | IR cm$^{-1}$ | NMR ppm |
|---|---|---|---|---|---|
| 1. | C$_{11}$H$_{10}$N$_2$OS | 52 | 116–117 (EtOH) | 2240 | 3.2–3.9/m, 4H, 2CH$_2$/ |
|  |  |  |  | 1665 | 4.8/s, 2H, CH$_2$/ |
|  | 218,26 |  |  | 1250 | 7.6/m, 4H, ArH/ |
| 2. | C$_{11}$H$_{10}$N$_2$OS | 45 | 84–85 (EtOH) | 2240 | 3.2–3.8/m, 4H, 2CH$_2$/ |
|  |  |  |  | 1665 | 4.6/s, 2H, CH$_2$/ |
|  | 218,26 |  |  | 1410 | 7.6/q, 4H, ArH/ |
| 3. | C$_{11}$H$_{10}$N$_2$OS | 48 | 77–78 (i-PrOH) | 2240 | 3.1–3.8/m, 4H, 2CH$_2$/ |
|  |  |  |  | 1670 | 4.5/s, 2H, CH$_2$/ |
|  |  |  |  | 750 | 7.6/s, 4H, ArH/ |
| 4. | C$_{11}$H$_{13}$NOS | 44 | oil* | 1665 | 1.5/d, 3H, CH$_3$/ |
|  |  |  |  | 1405 | 2.9–3.7/m, 4H, 2CH$_2$/ |
|  | 207,28 |  |  | 1240 | 5.4/q, 1H, CH/ |
|  |  |  |  | 788 | 7.3/s, 5H, ArH/ |
| 5. | C$_{16}$H$_{15}$NO$_2$S | 42 | 54–55 | 1660 | 3.0–3.7/m, 2H, 2CH$_2$/ |
|  |  |  |  | 1250 | 4.5/s, 2H, CH$_2$/ |
|  | 285,36 |  |  | 782 | 6.7–7.5/m, 9H, ArH/ |
| 6. | C$_{17}$H$_{17}$NO$_2$S | 61 | 98–99 | 1660 | 2.9–3.6/m, 4H, 2CH$_2$/ |
|  |  |  |  | 1252 | 4.4/s, 2H, CH$_2$/ |
|  | 299,38 |  |  | 788 | 5.0/s, 2H, CH$_2$/ |
|  |  |  |  | 760 | 7.1/q, 4H, ArH/ |
|  |  |  |  |  | 7.4/s, 5H, ArH/ |
| 7. | C$_{11}$H$_{10}$F$_3$NOs | 73 | 41–45 | 1665 | 3.0–3.7/m, 4H, 2CH$_2$/ |
|  |  |  |  | 1330 | 4.6/s, 2H, CH$_2$/ |
|  |  |  |  | 1240 | 7.5/q, 4H, ArH/ |
| 8. | C$_{11}$H$_{10}$F$_3$NOS | 56 | 41–42 | 1670 | 3.1–3.7/m, 4H, 2CH$_2$/ |
|  |  |  |  | 1417 | 4.7/s, 2H, CH$_2$/ |
|  |  |  |  | 1311 | 7.2–7.8/m, 4H, ArH/ |
| 9. | C$_{11}$H$_{10}$F$_3$NOS | 61 | olaj* | 1673 | 3.1–3.7/m, 4H, 2CH$_2$/ |
|  |  |  |  | 1408 | 4.6/s, 2H, CH$_2$/ |
|  |  |  |  | 1331 | 7.6/s, 4H, ArH/ |

*Purified by column chromatography with chloroform as eluent.

The invention is illustrated in detail by the following non-limiting Examples.

EXAMPLE 1

Preparation of 3-(2-cyanophenylmethyl)-2-thiazolidinone

A mixture containing 3.09 g (0.03 mol) of 2-thiazolidinone, 11.2 g (0.081 mol) of potassium carbonate, 1.8 g (0.018 mol) of potassium hydrogen carbonate, 0.5 ml (0.027 mol) of water and 6.47 g (0.033 mol) of 2-bromomethylbenzonitrile in 30 ml of methyl isobutyl ketone is refluxed for 5 hours, then cooled down. After adding 30 ml of water the mixture is stirred for 30 minutes, the insoluble precipitate is filtered off, washed twice with 10 ml of water each and dried. After recrystallizing 4.71 g of crude product from 20 ml of ethanol under simultaneous clarification with activated carbon 3.39 g (51.8%) of white, crystalline title compound are obtained, m.p.: 116°–117° C.

EXAMPLE 2

Preparation of a pharmaceutical composition containing 3-(2-cyanophenylmehyl)-2-thiazolidinone as active ingredient

| Ingredients: | g |
|---|---|
| 3-(2-Cyanophenylmethyl)-2-thiazolidinone | 40 |
| Lactose | 80 |
| Starch | 67 |
| Talc | 6 |
| Polyvinylpyrrolidone | 4 |
| Magnesium stearate | 2 |

From the above composition 1000 tablets weighing 200 mg each with a diameter of 8 mm are prepared.

We claim:

1. 2-Thiazolidinone derivatives of the formula (I),

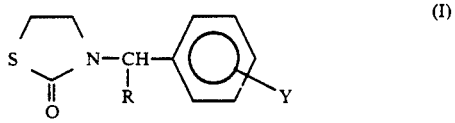

(I)

wherein
R means hydrogen or a C$_{1-4}$alkyl group; and
Y stands for cyano, trifluoromethyl, phenloxy or phenyl(C$_{1-4}$alkyl)oxy group.

2. 3-(2-Cyanophenylmethyl)-2-thiazolidinone.

3. A pharmaceutical composition, which comprises as active ingredient a 2-thiazolidinone derivative of the formula (I)

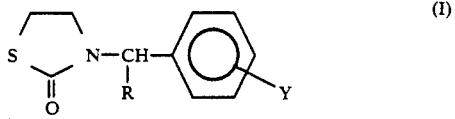

(I)

wherein
R means hydrogen or a C$_{1-4}$alkyl group; and
Y stands for cyano, trifluoromethyl, phenyloxy or phenyl (C$_{1-4}$alkyl)oxy group
in admixture with carriers and/or additives commonly used in the pharmaceutical industry.

4. A pharmaceutical composition, which comprises as active ingredient 3-(2-cyanophenylmethyl)-2-thiazolidinone in admixture with carriers and/or additives commonly used in the pharmaceutical industry.

5. A method of inhibiting gastric acid secretion in a patient in need thereof which comprises: orally administering to the patient an effective amount of a compound of the formula I as defined in claim 1.

6. A method of inhibiting gastric acid secretion in a patient in need thereof which comprises: orally administering to the patient an effective amount of the compound of claim 2.

* * * * *

UNITED STATES PATENT AND TRADEMARK OFFICE
CERTIFICATE OF CORRECTION

PATENT NO. : 5,169,859

DATED : December 8, 1992

INVENTOR(S) : SZABADKAI et al.

It is certified that error appears in the above-identified patent and that said Letters Patent is hereby corrected as shown below:

Claim 1, column 4, line 50: "phenloxy" should read -- phenyloxy --

Signed and Sealed this

Twenty-sixth Day of October, 1993

Attest:

BRUCE LEHMAN

Attesting Officer     Commissioner of Patents and Trademarks